US00PP12131P2

(12) United States Plant Patent
Lemon

(10) Patent No.: US PP12,131 P2
(45) Date of Patent: Oct. 9, 2001

(54) REGAL PELARGONIUM PLANT NAMED 'MONARCH'

(75) Inventor: David Lemon, Lompoc, CA (US)

(73) Assignee: John Bodger and Sons Company, South El Monte, CA (US)

( * ) Notice: Subject to any disclaimer, the term of this patent is extended or adjusted under 35 U.S.C. 154(b) by 0 days.

(21) Appl. No.: 09/120,156

(22) Filed: Jul. 21, 1998

(51) Int. Cl.[7] ..... A01H 5/00
(52) U.S. Cl. ..... Plt./331
(58) Field of Search ..... Plt./331

(56) References Cited

U.S. PATENT DOCUMENTS

P.P. 8,091 * 1/1993 Walters ..... Plt./331

* cited by examiner

*Primary Examiner*—Bruce R. Campell
*Assistant Examiner*—Wendy A. Baker
(74) *Attorney, Agent, or Firm*—Fulwider Patton Lee & Utecht, LLP

(57) ABSTRACT

The claimed cultivar is characterized by the clear pale purple flower which exhibits a dark maroon blotch presented over a medium green foliage. The overall effect of the flower is a bi-color presentation. Its superior performance is typified by its exceptionally fast rooting and finishing time, as well as its resistance to shattering.

1 Drawing Sheet

BACKGROUND OF THE NEW PLANT

The present invention comprises a new and distinct cultivar of *Pelargonium×domesticum* known by the varietal name 'Monarch' (Oglevee No. 761, Bodger No. 2 PD 33-7). The new variety was discovered in a selective breeding program by David Lemon at Bodger Seeds, Ltd., Lompoc, Calif. The new variety is a selection from the crossing of Oglevee No. 425 (unpatented) with Hazel Ripple (unpatented), both of which exhibit small lavender florets having veining on the petals as compared to the claimed cultivar which exhibits a clear lavender florets having a bold blotch of color.

The new cultivar was first asexually reproduced by cuttings at Oglevee Ltd., located at 152 Oglevee Lane, Connellsville, Pa., 15425 and has been repeatedly asexually reproduced by cuttings at Oglevee Ltd. in Connellsville, Pa. It has been found to retain its distinctive characteristics through successive propagations.

The new cultivar was grown in a glass greenhouse in Connellsville, Pa., using full light, 60° Fahrenheit night temperature, 68° Fahreheit day temperature, and grown in a soilless media using a constant fertilizer of 200–250 parts per million of Nitrogen and Potassium, in full light. The claimed plant was grown from a rooted cutting, potted in a 10 cm pot and exhibited a six week response time from the rooted cutting to a flowering plant.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings believed to have been potted in a 20 cm pot on approximately Jan. 15, 1996 and flowering on approximately Feb. 27, 1996, under full light in the greenhouse, and color readings were taken in the Oglevee office under 200–220 foot candles of cool white fluorescent light using The Royal Horticultural Society of London Colour Chart.

THE PLANT

Classification:
- *Botanical.*—*Pelargonium×domesticum.*
- *Commercial.*—*Regal Geranium 'Monarch'.*

Form: Upright medium mound habit.
- *Height.*—20–22 cm above the top of pot.
- *Growth.*—Medium plant habit; free basal branching.
- *Strength.*—Needs no artificial support; quick rooting.

Foliage: Slightly reflective; Medium green; Stalked leaf attachment.

Leaves:
- *Size.*—8.5–10.5 cm across when fully expanded.
- *Shape.*—Depressed ovate; truncate base.
- *Margin.*—Serrately lobed.
- *Texture.*—Pubescent; leathery.
- *Color.*—Top: Green Group 137B. Bottom: Yellow-Green Group 147B. Zone: None present.
- *Ribs and veins.*—Palmate venation. Color: Yellow-Green Group 146C.

Petioles:
- *Length.*—5.5–7.5 cm.
- *Color.*—*Yellow-Green Group* 146B.

Stem:
- *Color.*—Yellow-Green Group 146C.
- *Internode length.*—3.5–20 mm.

THE BUD (UMBEL)

This information refers to the stage of development when the peduncle has fully elongated and buds are just showing color.

Shape: Elliptical; cluster.

This information refers to the entire bud cluster. "Elliptical" refers to the shape of individual buds within the cluster. Number of buds per cluster is 6–12.

Size: 3.5–4.0 cm across; umbel depth 4.0–5.0 cm; buds not showing any color.

INFLORESCENCE

Blooming habit: Continuous flowering; Medium size florets forming full flower head; observed number of florets 6–12 per umbel.

Borne: Umbel; Floret on pedicel; pedicel on peduncle; 2.0–3.5 cm above foliage.

Closed florets: Bud Size: 1.6–2.0 cm long; 6.0–12 mm in width; bud just beginning to show color.

Size: Fully Open Bloom: 10.0–11.5 cm across.

Open florets:

*Form.*—Cupped; 5.5–6.0 cm across at the widest point.

*Color.*—Top: Upper two petals have Purple Group 77D outer edge and Red-Group 72A veining and streaking; center blotch is Greyed-Purple Group 187A; base is White Group 155D; Lower three petals are Purple Group 76D with White Group 155D base. Bottom: Upper two petals are Purple Group 76D with Blotch and veining showing through; Lower three petals are White Group 155D at the base and shading to Purple Group 76D. Eye: None

*Petals.*—5 in number.

*Size.*—3.5–4.0 cm in length; 3.0–3.5 cm in width.

*Texture and appearance.*—Satiny, slightly shiny ruffled bloom whose appearance at a distance is a delicate light purple flower accented with bold maroon blotch above medium green foliage.

Petaloids:

*Quantity.*—0 petaloids.

Pedicel:

*Length.*—2.5–3.0 cm.

*Color.—Yellow-Green Group* 146B.

Peduncle:

*Length.*—5.0–8.0 cm long.

*Color.*—Yellow-Green Group 146B.

Persistence:

*Disease resistance.*—No known special disease resistence compared with other Geraniums.

*Lasting quality.*—Slow to shatter and continuous blooming.

REPRODUCTIVE ORGANS

Stamens:

*Anthers.*—Length: 2.0–3.0 mm.

*Filaments.*—Length: 10–18 mm. Color: White to pale purple at tips.

*Pollen.*—Orange-Red Group 34C.

Pistils:

*Number.*—1.

*Length.*—1.5–2.0 cm.

*Stigma.*—Color: Red-Purple Group 59A; 5–6 parted.

*Style.*—Length: 1.5–1.7 cm.

Ovaries:

*Color.*—Yellow-Green Group 146D; Superior pubescent.

*Length.*—5.0–7.0 mm.

Fruit: None.

GENERAL CHARACTERISTICS

'Monarch' is a new and distinct addition to the Royalty Series and presents a pale purple flower with a striking maroon blotch over medium green foliage. The Royalty Series is an easy to grow plant characterized by vigorous upright growth habit, continuous flowering and abundant flowers. 'Monarch' has an improved rooting speed of only 21 days as compared to the variety Princess (U.S. Plant Pat. No. 8,091) which takes up to 28 days. Further, as compared to its parents, both of which are small lavender flowers which exhibit veining on the floret, 'Monarch' presents a clear lavender flower presented in a medium sized floret. Finishing time and post harvest production are also improved in this new cultivar.

I claim:

1. A new and distinct variety of Geranium plant, substantially as shown and described.

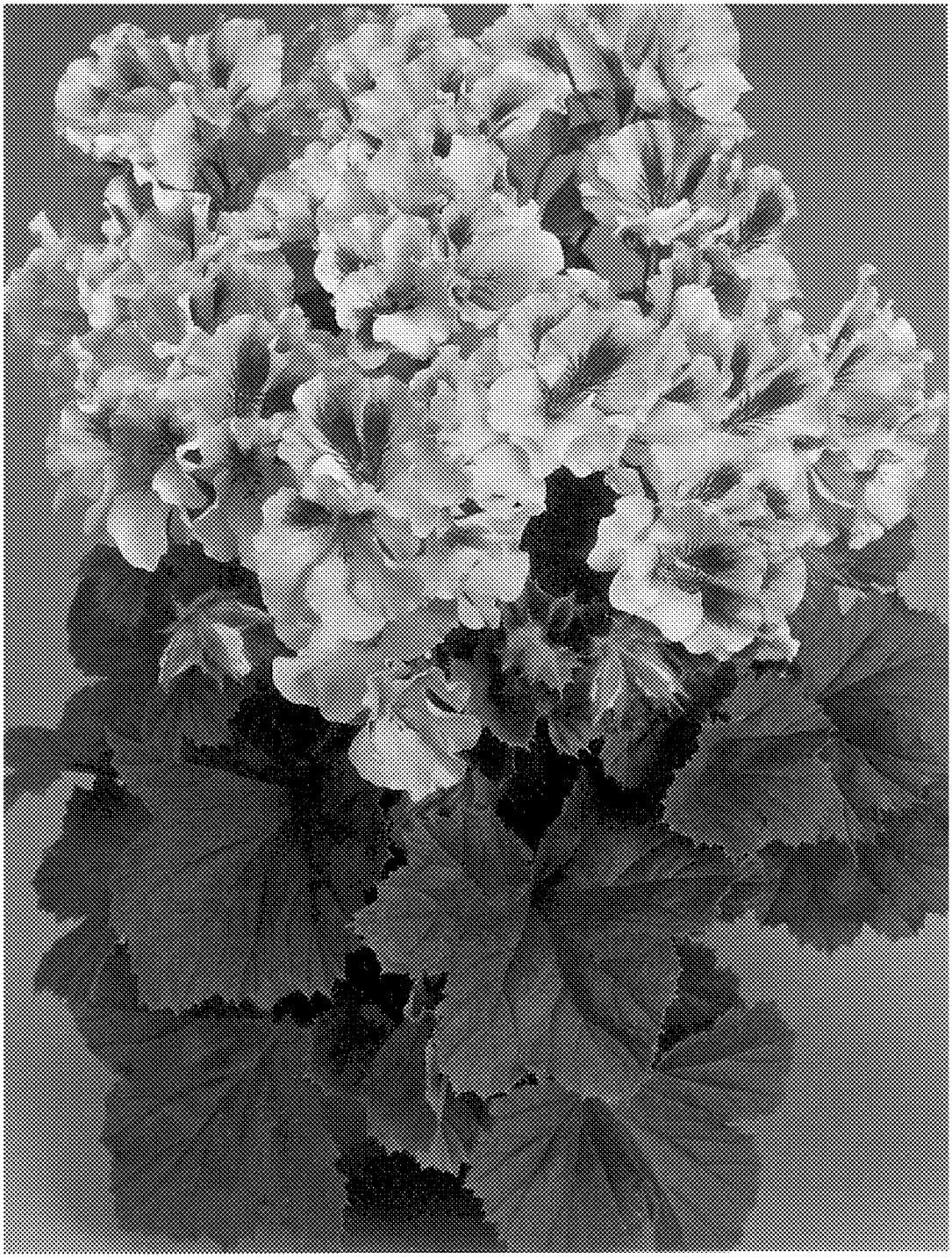

* * * * *